United States Patent

Burri et al.

[11] 4,087,488
[45] May 2, 1978

[54] CYANO-4-(0,0-DIALKYLPHOSPHORYLOX-Y)-CYCLOHEX-4-ENES

[75] Inventors: Kaspar F. Burri, West Caldwell, N.J.; Frank Kienzle, Therwill, Switzerland; Perry Rosen, North Caldwell, N.J.

[73] Assignee: Hoffman-La Roche Inc., Nutley, N.J.

[21] Appl. No.: 766,092

[22] Filed: Feb. 7, 1977

Related U.S. Application Data

[62] Division of Ser. No. 618,853, Oct. 2, 1975, Pat. No. 4,025,584, which is a division of Ser. No. 497,598, Aug. 15, 1974, Pat. No. 3,933,948.

[51] Int. Cl.² .......................................... C07F 9/117
[52] U.S. Cl. .................................................. 260/940
[58] Field of Search ........................................ 260/940

[56] References Cited

U.S. PATENT DOCUMENTS 3,954,919  5/1976  Kishino et al. .................... 260/940

*Primary Examiner*—Anton H. Sutto
*Attorney, Agent, or Firm*—Samuel L. Welt; George M. Gould; Raymond R. Wittekind

[57] ABSTRACT

Dienylphosphates of the formula

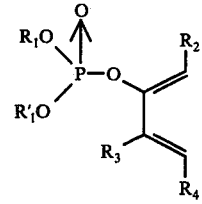

I wherein each of $R_1$ and $R_1'$ is lower alkyl, aryl or benzyl and each of $R_2$, $R_3$ and $R_4$ is hydrogen or lower akyl, are useful as anthelmintic agents and as intermediates for enolphosphates having anthelmintic activity.

4 Claims, No Drawings

CYANO-4-(0,0-DIALKYLPHOSPHORYLOXY)-CYCLOHEX-4-ENES

This is a division, of application Ser. No. 618,853 filed October 2, 1975, now U.S. Pat. No. 425,584, which in turn is a division of application Ser. No. 497,598, filed Aug. 15, 1974, now U.S. Pat. No. 3,933,948, granted Jan. 20, 1976.

DETAILED DESCRIPTION OF THE INVENTION

The present invention relates to a series of compounds, referred to as dienylphosphates, represented by the formula

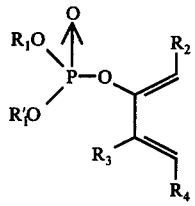

wherein each of $R_1$ and $R_1'$ is lower alkyl, aryl or benzyl and each of $R_2$, $R_3$ and $R_4$ is hydrogen or lower alkyl.

As used herein, the term "lower alkyl" refers to a monovalent substituent consisting solely of carbon and hydrogen having a straight chain of from 1 to 5 carbon atoms. The term "aryl" refers to phenyl or phenyl substituted with one or more lower alkyl, halo (fluorine, chlorine or bromine), nitro or lower alkoxy (lower alkyl linked through an ether oxygen) groups.

Depiction of dienes in the s-cis conformation is for convenience only, and does not necessarily represent the actual geometrical conformation at any particular time.

Preferred compounds falling within the above genus are those where $R_1$ and $R_1'$ are methyl or ethyl and $R_2$, $R_3$ and $R_4$ are hydrogen. Thus, particularly preferred compounds of the present invention are dimethyl (1,3-butadien-2-yl) phosphate [alternate nomenclature - dimethyl 1-vinylvinyl-phosphate]; and diethyl (1,3-butadien-2-yl) phosphate [alternate nomenclature - diethyl 1-vinylvinylphosphate].

Compounds of formula I may be prepared from readily available starting materials by simple chemical procedures.

Compounds of formula I where $R_2$, $R_3$ and $R_4$ are hydrogen and where $R_1$ and $R_1'$ are identical are prepared from 3,4-dichlorobutanone by reaction with a phosphite of the formula $$P(OR_1)_3 \qquad II$$

wherein $R_1$ is as above. Representative phosphites include trimethylphosphite, triethylphosphite, tri(n-propyl)phosphite, tri-(n-butyl)-phosphite, tri(n-pentyl)-phosphite, triphenylphosphite and tribenzylphosphite. Particularly preferred phosphites are trimethylphosphite and triethylphosphite.

The reaction is conveniently performed in the absence of solvents other than the reactants. However, if desired, inert organic solvents may be employed. Suitable inert organic solvents include, for example, hydrocarbons such as hexane, benzene and toluene; halogenated hydrocarbons such as dichloromethane, and the like.

The reaction appears to occur in two stages. The first stage occurs readily at temperatures from about 0° to about 50° C, preferably about 20° to 30° C, with the evolution of an alkyl chloride, $R_1Cl$. The final stage of the reaction involves the elimination of hydrogen chloride. This occurs by heating at a temperature of from about 50° to about 150° C, and is most conveniently carried out by distillation of the reaction mixture, preferably under reduced pressure. There is thus obtained the final product of formula I wherein $R_2$, $R_3$ and $R_4$ are each hydrogen.

To enhance the elimination of the hydrogen chloride during the distillation step, it is preferable to add a small quantity (for example, less than 1 mole %) of a Lewis acid such as aluminum chloride. To prevent polymerization of the diene of formula I during distillation, the addition of a small quantity (for example, 1 mole % or less) of a polymerization inhibitor such as hydroquinone is preferred.

The preparation of dienylphosphates from 3,4-dichlorobutanone and phosphites is indeed unexpected, since the identical reaction utilizing 3,4-dibromobutanone is known to afford exclusively methyl vinyl ketone, J. P. Schroeder, et al., J. Org. Chem. 35, 3181 (1970).

The full scope of compounds of formula I may be prepared by a different procedure, starting with a conjugated ketone of the formula

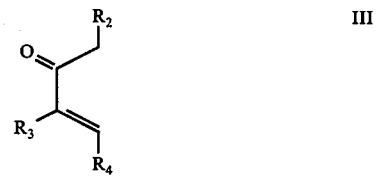

wherein $R_2$, $R_3$ and $R_4$ are as above.

This procedure involves, first, the conversion of the compound of formula III to its enolate of the formula

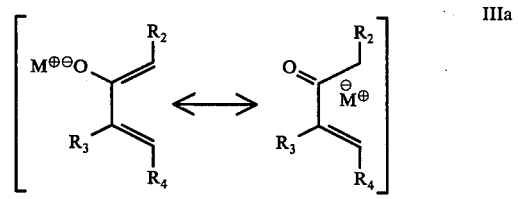

wherein $R_2$, $R_3$ and $R_4$ are as above and $M^+$ is the cation of sodium, potassium or lithium.

Conversion of the compound of formula III to its enolate is carried out by reaction of the ketone with a strong organic soluble alkali metal amide base in an inert organic solvent at a low temperature. Preferred bases are alkali metal alkyl or cycloalkyl amides such as lithium N-cyclohexyl N-isopropylamide, lithium cyclohexylamide; and alkali metal silylamides, such as sodium bis(trimethylsilyl)amide. The amide bases utilized in the present process may be prepared by methods well known in the art.

Suitable inert organic solvents for the present reaction include, for example, organic ethers, e.g., diethyl ether, dioxane and tetrahydrofuran; hydrocarbons such as hexane and heptane; and so forth.

The enolate, prepared in situ as hereinabove described, is then reacted with a halophosphate of the formula

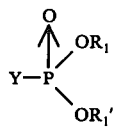 IV wherein $R_1$ and $R_1'$ are as above and Y is chlorine, bromine or iodine. Both the formation of the enolate and the subsequent reaction with the halophosphate may be suitably conducted at a reduced temperature, for example, from about $-80°$ to about $-20°$ C. A particularly preferred temperature range is from about $-65°$ to about $-75°$ C.

After standard workup conditions, the product of formula I is isolated and purified. A particularly preferred purification method involves distillation at reduced pressure. Among the compounds of formula I that may be prepared by this method there may be mentioned:

dimethyl (1,3-butadien-2-yl) phosphate
diethyl (1,3-butadien-2-yl) phosphate
dimethyl (1,3-pentadien-3-yl) phosphate
diethyl (1,3-pentadien-3-yl) phosphate
dimethyl (1,3-pentadien-2-yl) phosphate
diethyl (1,3-pentadien-2-yl) phosphate
dimethyl (3-methyl-1,3-butadien-2-yl) phosphate
diethyl (3-methyl-1,3-butadien-2-yl) phosphate
dimethyl (3-methyl-1,3-pentadien-2-yl) phosphate
diethyl (3-methyl-1,3-pentadien-2-yl) phosphate
dimethyl (2-methyl-1,3-pentadien-3-yl) phosphate
diethyl (2-methyl-1,3-pentadien-3-yl) phosphate
dimethyl (3-ethyl-1,3-hexadien-2-yl) phosphate
diethyl (3-ethyl-1,3-hexadien-2-yl) phosphate
dimethyl (2-ethyl-1,3-hexadien-3-yl) phosphate
diethyl (2-ethyl-1,3-hexadien-3-yl) phosphate
dimethyl (4-methyl-3,5-decadien-5-yl) phosphate
diethyl (5-ethyl -3,5-nonadien-4-yl) phosphate
dimethyl (4-methyl-2,4-decadien-3-yl) phosphate
diethyl (4-propyl-3,5-nonadien-5-yl) phosphate The compounds of formula I are substituted dienes and are highly reactive towards dienophiles in Diels-Alder reactions to form 1,4-cycloadducts (enol phosphates) of the formula

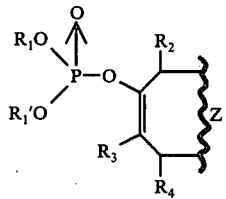 V wherein $R_1$, $R_1'$, $R_2$, $R_3$ and $R_4$ are as above and Z is the residue of a dienophile moiety.

For the purposes of this specification, a dienophile is defined as an unsaturated organic compound which will take part in a 1,4-cycloaddition reaction with a conjugated diene. Most dienophiles have a nonaromatic unsaturated (double or triple bond) linkage upon which there is directly substituted at least one electron withdrawing group. Among the types of dienophiles which may be mentioned are: nitriles, e.g., tetracyanoethylene and acrylonitrile; aldehydes, e.g., crotonaldehyde and acrolein; acids, e.g., acrylic acid, cinnamic acid, maleic acid and fumaric acid; esters, e.g., ethyl acrylate, dimethyl maleate, dimethyl fumarate, diethyl acetylenedicarboxylate, diethylazodicarboxylate; anhydrides, e.g., maleic anhydride and citraconic anhydride; imides, e.g., N-phenylmaleimide, 4-phenyl-1,2,4-triazoline-3,5-dione and p-phenylazomaleinanil; nitroso compounds, e.g., nitrosobenzene; nitro compounds, e.g., β-nitrostyrene and 1-nitropropene; ketones, e.g., methyl vinyl ketone; and so forth.

Preparation of Diels-Alder adducts from compounds of formula I is carried out according to the usual methods well known in the art for such reactions. Thus, the Diels-Alder reaction is conveniently performed by admixture of a diene (the compound of formula I) with a dienophile.

The reaction may be carried out in the absence of any solvent, or an inert organic solvent may be utilized. Suitable inert organic solvents that may be mentioned include, for example, hydrocarbons such as hexane, heptane, benzene and toluene; halogenated hydrocarbons, such as dichloromethane; organic ethers, such as diethyl ether, tetrahydrofuran and dioxane; and the like. The Diels-Alder reaction may be carried out over a wide range of temperature conditions from about 0° to about +150° C. A preferred temperature range is from about 20° to about 70° C.

The dienylphosphates of formula I are useful as anthelmintic agents. Furthermore, the enolphosphates of formula V also have anthelmintic properties. Thus, the compounds of formula I are additionally valuable as intermediates for the preparation of compounds of formula V.

Specifically, these compounds are effective, upon oral administration (0.1% in feed) in the control of *Ascaris suum* infection in mice.

Compounds of formula I, as has been demonstrated hereinabove, are also useful as reagents in organic synthesis as diene moieties for use in Diels-Alder reactions for the construction of more complex organic molecules.

Additionally, dienes of formula I serve as valuable monomers which may be either self-polymerized, or co-polymerized with monomers well known in the art, to prepare complex polymeric structures having a variety of useful properties, for example as flame retardants.

The preparation of compounds of formulas I and V, as well as processes therefor, are illustrated by the following specific examples. These examples are illustrative only of the invention and are not to be construed as limitative thereof in any manner.

EXAMPLE 1

3,4-Dichlorobutanone

Chlorine was introduced into a solution of 140 g (1 mole) of methyl vinyl ketone in 600 ml of chloroform with ice-cooling. When 142 g of chlorine (1 mole) had been absorbed, the chloroform was evaporated (bath temperature <35°) leaving 290 g of slightly impure 3,4-dichlorobutanone which was used without further purification.

EXAMPLE 2

Diethyl 1-vinylvinylphosphate hemihydrate

Triethyl phosphite (166 g, 1 mole) was cooled in an ice bath and 3,4-dichlorobutanone (140 g, 1 mole) was added. The mixture was stirred under nitrogen atmosphere for 2 hr at 0° then for 20 hr at room temperature. After 0.5 g of hydroquinone and 0.5 g of aluminum chloride had been added, the mixture was distilled in vacuo to give 34.4 g of pure diethyl 1-vinylvinylphosphate hemihydrate, bp 91°-92°/2 mm.

Anal. Calcd. for $C_8H_8PO_4 \cdot 1/2 H_2O$ (215.19): C, 44.75; H, 7.49 Found: C, 45.14; H, 7.40

EXAMPLE 3

Dimethyl 1-vinylvinylphosphate

Trimethyl phosphite (28.6 g) was treated with 3,4-dichlorobutanone (32 g) using the identical procedure as in Example 2. Distillation gave pure dimethyl 1-vinylvinylphosphate, bp 79°-83°/1.5 mm.

Anal. Calcd. for $C_6H_{11}PO_4$ (178.13): C, 40.46; H, 6.23 Found: C, 39.83; H, 6.25 UV 220 nm ($\epsilon$ 16520) in methanol.

EXAMPLE 4

1,1,2,2-Tetracyano-4-(O,O-diethylphosphoryloxy)cyclohex-4-ene

To a solution of 2.15 g (0.01 mole) of diethyl 1-vinylvinylphosphate in 10 ml of tetrahydrofuran was added under a nitrogen atmosphere 1.28 g (0.01 mole) of tetracyanoethylene. The yellow solution was left standing at room temperature for 2 days before it was evaporated. The residual syrup was taken up in ethyl acetate. Petroleum ether was added to incipient turbidity and the mixture was stored at 0° for 5 days. Filtration gave 2.10 g of 1,1,2,2-tetracyano-4-(O,O-diethylphosphoryloxy)-cyclohex-4-ene, mp 97°-98°. Recrystallization from ethyl acetate-petroleum ether afforded long prisms and short plates of pure material both having mp 98°.

Anal. Calcd for $C_{14}H_{14}N_4O_4P$ (333.27): C, 50.46; H, 4.23; N, 16.81 Found: C, 50.61; H, 4.54; N, 16.98 IR (Nujol mull): $\nu$max 1665, 1260 and 1045 cm$^{-1}$.

NMR (CDCl$_3$), $\tau$: 8.61 (triplet, 6H); 6.69 (multiplet, 4H); 5.75 (quintet, 4H), 4.12 (multiplet, 1H).

EXAMPLE 5

4-(O,O-Dimethylphosphoryloxy)-cyclohex-4-en-cis-1,2-carboxylic anhydride

A mixture of 0.98 g (0.01 mole) of maleic anhydride and 1.78 g (0.01 mole) of dimethyl 1-vinylvinylphosphate in 50 ml of benzene was stirred at room temperature for 20 hr. Evaporation gave a syrup which crystallized from ethyl acetate-petroleum ether to give 0.810 g of 4-(O,O-dimethylphosphoryloxy)-cyclohex-4-en-cis-1,2-carboxylic anhydride, mp 71°-72°. Recrystallization from the same solvent system gave prisms, mp 73°-74°.

Anal. Calcd for $C_{10}H_{13}O_7P$ (276.18): C, 43.49; H, 4.74 Found: C, 43.44; H, 4.71 IR (Nujol mull): 1850, 1785, 1670, 1275 and 1045 cm$^{-1}$.

EXAMPLE 6

2-Phenyl-4(O,O-diethylphosphoryloxy)-3,6-dihydro-2H-1,2-oxazine

To a solution of 3.24 g (0.03 mole) of nitrosobenzene in 150 ml of methylene chloride was added 6.25 g (0.029 mole) of diethyl 1-vinylvinylphosphate. The mixture was left standing at room temperature for 20 hr before it was evaporated. The remaining crude product was purified on a silica gel column and eluted with ethyl acetate-petroleum ether, 1:2 to give 7.1 g of slightly colored 2-phenyl-4(O,O-diethylphosphoryloxy)-3,6-dihydro-2H-1,2-oxazine.

Anal. Calcd for $C_{14}H_{20}NO_5P$ (313.30): C, 53.67; H, 6.43; N, 4.47 Found: C, 53.52; H, 6.57; N, 4.26 UV (ethanol); 240 ($\epsilon$ 7880), 282 nm ($\epsilon$ 850). NMR (CDCl$_3$), $\tau$: 6.15 (s), 5.50 (m), 4.25 (m).

EXAMPLE 7

1-Acetyl-3-(O,O-dimethylphosphoryloxy)cyclohex-3-ene and
1-acetyl-4-(O,O-dimethylphosphoryloxy)cyclohex-3-ene Dimethyl 1-vinylvinylphosphate (1.78 g) was dissolved in 30 ml of methyl vinyl ketone and stirred for 20 hr at 65° under an atmosphere of nitrogen. The excess methyl vinyl ketone was evaporated off to give 3.60 g of crude product which was purified by column chromatography.

Anal. Calcd for $C_{10}H_{17}PO_5$ (248.22): C, 48.39; H, 6.91 Found: C, 48.58; H, 7.00
The position of the acetyl peaks in the NMR spectrum indicated that the product was a mixture of isomers.

EXAMPLE 8

Preparation of 2-phenyl-6(O,O-diethylphosphoryloxy)-2,3,5,8-tetrahydro-1H-s-triazolo[1,2a]pyridazine-1,3-dione A benzene solution of equivalent amounts of diethyl-1-vinylvinylphosphate and 4-phenyl-1,2,4-triazoline-3,5-dione is allowed to stand at room temperature for 10-20 hrs. The solvent is separated, and the residue is crystallized from benzene-hexane to give colorless crystals of product, m.p. 84°-85°.

Anal. Calcd. for $C_{16}H_{20}H_3O_6P$ (381.33): C, 50.40; H, 5.29; N, 11.01; P, 8.12 Found: C, 50.58; H, 5.27; N, 11.14; P, 8.10

EXAMPLE 9

Preparation of diethyl 1-vinylvinylphosphate from methyl vinyl ketone

A solution of 31 g (0.22 moles) of N-cyclohexyl N-isopropylamine in 400 ml of tetrahydrofuran is cooled to $-70°$. To the stirred solution, 0.22 moles of n-butyllithium in hexane are added dropwise over a 5 min. period, followed by 14 g (0.20 moles) of methyl vinyl ketone during a 20 min. period, followed by 37.8 g (0.22 moles) of diethyl chlorophosphate during a 10 min. period. After an additional 90 min. at $-70°$, the solution is allowed to warm to room temperature. It is diluted with methylene chloride, and then washed sequentially with 5% aqueous NaHCO$_3$, 1 N aqueous HCl, and 10% aqueous NaCl solution. The organic phase is dried and evaporated, and the residue distilled to yield 22-25 g diethyl 1-vinylvinylphosphate, b.p. 74°/0.5 mm.

We claim:
1. A compound of the formula

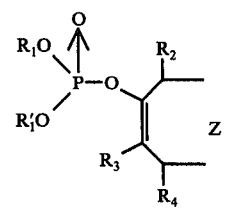

wherein each of $R_1$ and $R_1'$ is lower alkyl, aryl or benzyl, each of $R_2$, $R_3$ and $R_4$ is hydrogen or lower alkyl and Z is the residue of a dienophile moiety selected from the group consisting of tetracyanoethylene.

2. The compound of claim 1 wherein $R_1$ is methyl or ethyl.

3. The compound of claim 1 wherein each of $R_2$, $R_3$ and $R_4$ is hydrogen.

4. The compound of claim 3 which is 1,1,2,2-tetracyano-4-(O,O-diethylphosphoryloxy)-cyclohex-4-ene.